United States Patent [19]

Ekins

[11] Patent Number: 5,304,498
[45] Date of Patent: Apr. 19, 1994

[54] METHOD AND COMPOSITION FOR FREE LIGAND ASSAY

[76] Inventor: Roger P. Ekins, 56 Winchester Street, London, England

[21] Appl. No.: 707,434

[22] Filed: May 28, 1991

Related U.S. Application Data

[63] Continuation of Ser. No. 569,378, Aug. 13, 1990, abandoned, which is a continuation of Ser. No. 290,819, Dec. 22, 1988, abandoned, which is a continuation of Ser. No. 784,712, Oct. 4, 1985, abandoned, which is a continuation of Ser. No. 548,886, filed as PCT/GB83/00078, Mar. 17, 1983, abandoned.

[30] Foreign Application Priority Data

Mar. 19, 1982 [GB] United Kingdom ............... 8208043

[51] Int. Cl.$^5$ ............... G01N 33/566; G01N 33/53; G01N 33/543; G01N 33/551

[52] U.S. Cl. ............... 436/501; 436/500; 436/518; 436/524; 436/528; 436/529; 436/804; 436/828

[58] Field of Search ............... 436/500, 501, 828, 804, 436/529, 518, 524, 528

[56] References Cited

U.S. PATENT DOCUMENTS

| | | | |
|---|---|---|---|
| 4,200,436 | 4/1980 | Mochida et al. | 436/529 X |
| 4,292,296 | 9/1981 | Parsons, Jr. | 436/500 |
| 4,366,143 | 12/1982 | Midgley et al. | 436/501 |
| 4,410,633 | 10/1983 | Hertl et al. | 436/800 X |
| 4,426,453 | 1/1984 | Cree et al. | 436/804 X |
| 4,430,318 | 2/1984 | Langone | 436/828 X |
| 4,481,298 | 11/1984 | Cone, Jr. et al. | 436/500 |
| 4,745,072 | 5/1988 | Ekins et al. | 436/804 X |

OTHER PUBLICATIONS

Dans et al (1980) Microbiology 3rd Ed, Harper & Row, Philadelphia, pp. 326–328.
Spencer CA. J. Endocrinol. Invest. 9 (Suppl. 4) 1986, pp. 57–66.
Alexander, NM. Clin. Chem. 32 (3), 1986, p. 417.

*Primary Examiner*—Christine M. Nucker
*Assistant Examiner*—David R. Preston
*Attorney, Agent, or Firm*—Dann, Dorfman, Herrell and Skillman

[57] ABSTRACT

A method for determining the amount of free ligand in a test ample where the ligand is also present bound to one or more endogenous receptors, comprising combining the test sample, ligand receptor and unlabelled, differential binding ligand analogue, incubating to permit the free ligand and unlabelled, differential binding ligand analogue to compete for the ligand receptor separating the ligand analogue, determining the amount of ligand receptor bound to the ligand or to the ligand analogue, and correlating the amount of bound ligand receptor to the amount of free ligand present in the test sample.

17 Claims, No Drawings

METHOD AND COMPOSITION FOR FREE LIGAND ASSAY

This is a continuation of copending application Ser. No. 569,378, filed Aug. 13, 1990, now abandoned, which is a continuation of abandoned application Ser. No. 290,819, filed Dec. 22, 1988, which is a continuation of abandoned application Ser. No. 784,712, filed Oct. 4, 1985, which is a continuation of abandoned application Ser. No. 548,886, filed as PCT/GB83/00078, Mar. 17, 1983.

BACKGROUND OF THE INVENTION

This invention relates to direct, specific binding assays for free ligands in test samples where the ligand is also found sequestered to endogenous receptors. This invention particularly relates to immunoassays for free thyroxine in test samples containing thyroxine binding proteins such as TBG and albumin.

Free ligands are defined for the purposes here as substances, usually of low molecular weight but not necessarily, which are present unbound in a test sample which contains an endogenous receptor for the ligand. The biological role for such receptors has not been definitively established; it is likely that they serve as carriers for the ligand, thereby creating a reservoir of the ligand which can dissociate by mass action as the free ligand is consumed in biological processes. Typically all but a small percentage of the ligand is present bound to its receptors.

Such receptors are typically proteins. The receptors may be specific, as in the case of autoantibodies, transcortin and TBG, or relatively nonspecific, for example albumin. The term endogenous does not mean that the receptor normally occurs in patient sample or is even of biological origin. It means only that the test sample as it is obtained from the patient is expected or potentially may contain a receptor which is binding some proportion of the ligand of interest.

Astute clinicians are turning increasingly to free ligand assay in an effort to more accurately assess the status of their patients. This effort has been facilitated by the appearance in the marketplace of so-called direct immunoassays for free ligands, more specifically free thyroxine immunoassays. Direct ligand assays are characterized by the measurement of the free ligand itself, rather than by other determinations which are then correlated to the free ligand concentration by calculations such as in the free thyroxine index.

Two techniques now exist for direct free ligand assay aside from equilibrium dialysis, a technique not particularly well suited to speedy and routine clinical laboratory use. In both techniques the free ligand is bound to a receptor included in the test kit and the amount of bound ligand is then determined. The methods differ in the manner in which the endogenous receptor present in the test sample is prevented from interfering in the assay. In the method of British Patent Application 2,030,290 the endogenous receptor is excluded by physically separating the test sample residue from the test receptor-bound ligand after adsorption of the free ligand from the test sample, i.e., by incubating test sample with insolubilized antibody for ligand, decanting the test sample residue, washing, adding tracer-labelled ligand and measuring the amount of tracer taken up by the antibody (which in turn is inversely proportional to the amount of ligand which bound to the test receptor). This method is commercially advantageous because it employs simple, pre-existing reagents. Radiolabelled thyroxine, which has been used for some time in total thyroxine tests, is satisfactory for use in the above-described direct free thyroxine assay as well. However, each ligand assay requires an analogue of that ligand and no labelled immuno reagent common to all ligand assays could be employed.

The direct free ligand assay described in European Patent Application 0 026 103 uses another system for neutralizing the potential interference by endogenous receptors. Rather than excluding the endogenous receptors from interaction with labelled ligand analogue by washing the receptors out of the system, the ligand analogue is chemically excluded from binding to the endogenous receptor. This is accomplished by using as ligand analogue a derivative of the ligand which binds insubstantially to endogenous receptor but which does bind comparatively well to test receptor. This derivative will for convenience be termed a differential binding ligand analogue hereinafter. This assay for free ligand has the advantage that it does not require an intermediate washing step. It does, however, require the special synthesis of a carefully designed tracer for each and every different ligand to be assayed.

Since it is believed that in the future a variety of ligands will be assayed by such direct methods, it would be commercially desirable to use common reagents among the assays if possible, the advantages including ease of manufacture, stability and improved assay performance.

Accordingly, it is an object of this invention to simplify reagent preparation in direct assays for free ligands.

The present invention provides a method for determining the amount of free ligand in a test sample where the ligand is also present bound to one or more endogenous receptors, comprising combining the test sample, ligand receptor and unlabelled differential binding ligand analogue, incubating to permit the free ligand and unlabelled, differential binding ligand analogue to compete for the ligand receptor separating the ligand analogue, determining the amount of ligand receptor bound to the ligand or to the ligand analogue, and correlating the amount of bound ligand receptor to the amount of free ligand present in the test sample.

The invention also resides in a composition for use in the assay of test samples containing free ligand and endogenous receptors for such ligand, comprising the ligand covalently conjugated to a substantially water insoluble substrate or to a water soluble substance physically adsorbed onto a substantially water insoluble substrate, said ligand being conjugated so as to substantially exclude the binding to such insoluble ligand of receptors for such ligand present in said test samples.

The invention, therefore, dispenses with the labelled, differential binding ligand analogue called for in the above-mentioned European Patent Application. Instead, the test receptor is directly or indirectly labelled. As will be explained below, it is now possible to contemplate a multipurpose or universal tracer, i.e. one which has common utility in all free ligand assays.

The assay method of this invention employs two principal reagents: First, the differential binding ligand analogue which is insolubilized or can be made so as part of the analytical procedure and, second, a labelled ligand antibody or an unlabelled ligand antibody conjugated to a labelled anti-(ligand antibody).

The differential binding ligand analogue comprises a residue of the ligand capable of binding anti-ligand antibody or other anti-ligand test receptor to the relative exclusion of endogenous receptor, which is covalently linked to a substantially water insoluble substance or, more conveniently, covalently linked to a substantially water soluble component which is (a) physically adsorbed onto an insoluble substrate or (b) further reacted to form a substantially water insoluble material.

The assay is conducted by combining the test sample, ligand antibody and unlabelled, differential binding ligand analogue, incubating to permit the free ligand and unlabelled, differential binding ligand analogue to compete for the ligand antibody, determining the amount of ligand antibody bound to the ligand or to the ligand analogue, and correlating the amount of bound ligand antibody to the amount of free ligand present in the test sample.

DETAILED DESCRIPTION OF THE INVENTION

The starting material for making the differential-binding ligand analogues used herein are those ligand analogues known in the art to bind proposed test ligand receptors such as antibodies but which comparatively do not bind endogenous ligand receptors. Suitable examples are disclosed in the above-mentioned European Patent Application and references cited therein.

The key to making suitable starting materials is to determine which sites on the ligand are comparatively necessary for binding to the expected endogenous receptor, and to then use those sites as linking groups to modifiers. This determination is ordinarily accomplished by modifying the charge, polar or steric outline of the ligand at various positions on the ligand and measuring the degree of adsorption of the modified ligand to receptor which has preferably been stripped of ligand, e.g., by charcoal adsorption of ligand. Determining the degree of adsorption will be within the skill of the artisan. For example, ligand containing a radioactive atom, e.g., $^{14}C$ or $^{3}H$, may be modified at various positions generally as described above. The mixture of receptor and ligand is incubated and, afterwards, dialyzed to remove unbound ligand. If little or no radioactivity is found in the dialysand then the modified ligand is a good candidate for a suitable starting material.

The ligand may be modified in any number of ways which may be expected to influence its binding to endogenous receptor. Since such binding is a function of the charge and steric profile of the ligand, modifying these profile characteristics will frequently change the affinity of the ligand for its endogenous receptor. The modifications may increase or decrease the affinity, or leave it largely unchanged. Thus, it is desirable in most cases to actually test for the changes in affinity as described above or otherwise as known in the art.

Suitable exemplary ligand modifications are disclosed in the European Patent Application cited above. As examples, the ligand may be substituted onto a large molecule such as a protein or synthetic polymer. The bulky substitution sterically (and perhaps by charge effects as well) impedes the binding of endogenous receptor to the ligand analogue.

Alternatively, optical isomers may be employed which will not bind endogenous receptors.

Another alterative is to modify the charge or polarity of the group or groups which participate in binding to endogenous receptors. For example, carboxy groups may be reacted to form ethers or amides, amino groups may be amidated, and charged sites can be methylated.

Any one or more of the above modifications can be made at once, but generally it is preferable to make only one modification at a time.

In the case of thyroxine, suitable starting materials include either D-thyroxine or thyroxine covalently joined to protein through amide bonds at the thyroxine carboxyl or amino radicals. The latter is preferred.

Once a suitable non-binding modified ligand is foudn a test receptor must be obtained which can bind both the sample ligand adn the proposed ligand analogue. Receptors suitable for use in this invention include antibodies or naturally occurring protein binder isolated from suitable biological carriers such as protein A from S. aureus.

Water soluble, protein-substituted ligands are preferred for use as the starting material for making water insoluble, differential binding ligand analogues because techniques for insolubilizing proteins are in wide-spread and conventional use in the immunoassay art. The protein component of the ligand analogue may be insolubilized before or after incubation with labelled ligand receptor during the assay procedure, although it is preferred to insolubilize the ligand-substituted protein before conducting the assay. This may be accomplished by a variety of methods, including preferably just adsorbing it onto the internal wall of a polyolefin test tube in accordance with known methods. The protein may alternatively be cross-linked with an agent such as glutaraldehyde and then adsorbed onto the test tube wall.

The ligand-substituted proteins may be insolubilized after the assay procedure by immuno precipitation with anti-protein in the presence of polyethylene glycol.

Alternatively, the ligand can be covalently bonded directly to an insoluble substrate through the group or groups previously found to be important in the binding of endogenous receptor. Suitable techniques are well known from the affinity chromatography art.

Protein-substituted ligands are also preferred because they can be used also as immunogens for making antibodies which will function as receptors in the test. Protein-substituted ligands in general are well known as immunogens for use in conventional procedures for producing antisera in the therapeutic and diagnostic arts. Their synthesis and use are within the skill of the ordinary artisan. However, it should be clear that only those protein-substituted ligands which bind poorly or not at all to endogenous receptors are of use in this invention.

The ligand made be modified in other ways than by linking to a protein. In such a case the test receptor (antibody) may be made in the fashion suggested in the above-cited European Patent Application, i.e., by raising an antiserum against an immunogen which is at least structurally homologous with the differenital binding ligand analogue.

The anti-ligand antibody is preferably purified from the harvested serum. This is conventional, and will generally entail techniques such as precipitation with ethanol or polyethylene glycol to separate the immunoglobulins, followed by affinity chromatography on insoluble, differential binding ligand analogue. Alternatively, a hybridoma may be produced from cells of the antibody-producing clone. The antibody should have an equilibrium constant on the order of $10^{11}$ liters/mole.

The purified antibody may they be labelled with a detectable group such as an enzyme, fluorescent group, chemiluminescent group or radioactive atom. However, it is preferred to label a stock antisera or antibody raised against the serum of the species of animal in which the anti-ligand antibody was raised. This labelled second antisera is a universal tracer reagent in that it can be used in any free ligand assay. Such a reagent would not be practical in the method of British Patent Application No. 2,030,290 because antibody could not effectively bind small molecule ligands which had been already bound by insoluble receptor. For the same reason such a reagent could not be used universally in the method or European Patent Application 0 026 103 because most ligand analogues that are disclosed are small molecules. Even as to the disclosed protein-substituted ligands, the sites of the substitution would change depending upon the ligand so that no one antiserum could be used universally.

The amount of anti-ligand antibody used in the assay should be less than the total of the free ligand expected in the samples to be assayed and the apparent concentration of ligand as insolubilized differential binding ligand analogue. This is best determined by assaying a panel of test samples having a wide range of known free ligand concentrations using various dilutions of anti-ligand antibody until the most satisfactory dose-response curve is obtained.

The amount of differential binding ligand analogue, the capacity and affinity of labelled receptor, the temperature and time of incubation and other parameters of the method herein are to be determined in each case by routine experimentation conventional in the art. In short, this entails adjusting the parameters until a suitable dose-response curve is obtained over the range of free ligand concentration expected in test samples. It is inherent in practicing the free ligand assay described herein that the ligand receptor has a dissociation constant, with respect to its binding to the ligand, within a factor of ten times more or less than the amount of free analyte, as those skilled in the art will readily appreciate from the following formula.

The amount of work required to optimize the assay in each case can be reduced by making advance estimates of some parameters in accordance with this formula $$b^2 - b\left[\frac{[fH]}{[R^*]} + \frac{1}{K_R[R^*]} + S + 1\right] + S = 0$$

where
[fH] = concentration of free ligand at equilibrium (as can be determined by equilibrium dialysis);
[R*] = concentration of labelled receptor;

$$S = \frac{\text{apparent concentration of insoluble ligand analogue}}{\text{concentration of labelled receptor}}$$

$K_R$ = equilibrium constant of receptor binding sites; and
b = fraction of labelled antibody bound to insoluble differential binding ligand analogue.

The response curve can be determined from this equation, but is assumes a single order of antibody binding sites and identical avidity of labelled receptor for free ligand and insoluble ligand analogue. The latter in particular is not likely to occur in most circumstances so the equation should be considered a time and experimentation-saving guide. The parameters will necessarily have to be optimized for optimal assay performance by experimental efforts.

EXAMPLE 1

This example describes a representative free ligand assay. The free ligand determined is L-thyroxine.

Preparation of Purified Radiolabelled Anti-Thyroxine Antibodies

L-thyroxine methylester was conjugated to bovine serum albumin by carbodiimide using methods known per se. The immunogen was injected into rabbits and the antiserum harvested. The immunoglobulin fraction antiserum was purified to the immuinoglobulin fraction by exclusion from binding to DEAE (diethylamino ethyl) cellulose using the following procedure. 1 ml of antiserumn was diluted with 3 ml of water and added to 8 gms. of wet, water-washed DEAE cellulose. After 1 hour incubation at 37° C., the supernatant liquid was removed by filtration and combined with the supernatant obtained from four washes of the DEAE cellulose with 5 ml portions of 10 mMolar phosphate buffer pH 8.0. The combined supernatant was concentrated to a final concentration of 8 mg/ml by pressure ultrafiltration.

An affinity column for purification and iodination of the crude antibody was prepared as follows. To 10 ml of washed, packed amino derivatized Sepharose (AH-Sepharose 4B; Pharmacia; Upsalla, Sweden) was added 10 ml of a 50% aqueous dimethylformamide (50% DMF) into which has been added 52 mg of thyroxine free acid. The pH was adjusted to 4.5 by addition of dilute HCl. To this was added dropwise, over 5 minutes, 3 ml of water to which had been added 500 mg of 1-ethyl-3-(3-diethylamine) propyl carbodiimide. After 20 hours tumbling at room temperature the derivatized Sepharose was washed with sufficient volumes of 50% DMF and then with water and finally suspended in 25 mMolar phosphate buffer, pH 7.4.

Purification and iodination of the anti-thyroxine antibodies was performed as follows. To 2 ml of packed thyroxine-derivatized Sepharose was added 4 ml of 25 mM phosphate buffered saline, pH 7.4, and 200 ul of purified anti-thyroxine containing rabbit immunoglobulins. The mixture was tumbled for 48 hours at room temperature and then washed twice with portions of 12 ml of 10 mM phosphate buffer, pH 7.4. 1 ml of the Sepharose was retained for later use. 2.0 ml of a 0.5 molar phosphate buffer pH 7.4 was added to the other mililiter of wet gel, followed by luCi of $^{125}$I (amersham, U.K.) in 10 ul sodium hydroxide. Then 40 ml of a fresh 7 mg/ml aqueous solution of chloramine T was added. After 60 sec. mixing at room temperature, 80 μl of a fresh aqueous solution of sodium metabisulfite was added. The iodinated gel was added on top of 3 ml of Bioget P2 (Bio Rad; Richmond, Calif.) packed in a glass column. The retained mililiter of uniodinated gel was likewise placed in a column. Both columns were eluted using the same technique: The column was washed with 25 ml of 10 mM phosphate buffer, pH 7.4, then 20 ml of 0.1 M disodium citrate. Then 100 ml of gradient was applied consisting of a linear mixture of 0.1 M disodium citrate (50 ml) and 0.1 M hydrochloric acid (50 ml). Fractions were collected directly into 0.5 M phosphate buffer pH 7.4 With respect to the iodinated gel column, fractions eluting between pH 2.5 and 1.5 contained peak radioactivity and were pooled. Analysis of fractions from the non-radiolabelled antibody column showed high specificity antibodies with an equilibrium association constant of $3.0 \times 10^{11}$ $M^{-1}$. The specific activity of the radiolabelled antibody was $2.85 \times 10^7$ mci/mmole.

Preparation of Insoluble, Differential Binding Thyroxine Ligand Analogue 1.0 gram of L-thyroxine was dissolved in 20 ml of dimethylsulfoxide and to this was added two equivalents of N-methylmorpholine. 400 mg of disuccinimidyl suberate (DSS, Pierce Chem. Co., N.J.) was added to this solution and mixed at room temperature for 30 minutes. This solution as then added to a solution of 2 grams of boviner serum albumin (BSA) dissolved in 400 ml of 50% DMF whose pH had been adjusted to 10.0 by the addition of sodium hydroxide solution. The mixture was stirred for 2 hours at room temperature and the pH maintained at 10.0 by dropwise addition of sodium hydroxide solution. The solution was then dialyzed against two changes of 2 liters of 50% DMF for 48 hours at 4° C., then dialysed overnight at 4° C. against 6 liters of 0.1 mM sodium hydroxide solution, and finally at 4° C. against five changes at eight hour intervals of six liters of water. The resulting dialysand was lyophlyized to dryness.

Sephadex G100 (Pharmacia; Upsalla, Sweden) was equilibrated in 25 mM phosphate buffer, pH 7.4, (PHOS), poured into glass column, washed with 200 ml of a 1% BSA solution in PHOS, and finally washed with PHOS until no further protein eluted. 10 mg of L-thyroxine-DSS-BSA conjugate was dissolved in 1 ml of PHOS and then eluted with PHOS. Four proteinacious peaks were observed. The last two peaks to elute were pooled and concentrated by lyophylization. Iodination of a portion of this material was performed by the chloramine-T method and was found not to bind to serum proteins in serum previously charcoal stripped to remove thyroid hormones. The material did displace $^{125}$I-thyroxine from purified anti-thryoxine antibodies as was demonstrated by standard second antibody separation radioimmunoassay methods.

The solid phase antigens was prepared from the L-thyroxine-DSS-BSA conjugate as follows: Sepharose 4B (Pharmacia, Sweden) was activated with cyanogen bromide by the method of Cuatrecasas (Cuatrecasas, P., J. Bio. Chem., 245, 3059, (1970)). To 1 ml of activated Sepharose was added 0.1 mg of lyophylized L-thryoxine-DSS-BSA which had been dissolved in 10 ml of 0.1 M phosphate buffer, pH 6.5. After reaction at room temperature for 16 hours the Sepharose-bound L-thyroxine-DSS-BSA conjugate was extensively washed with 50% DMF and then water, and finally resuspended in 10 ml of 25 mMolar phosphate buffer, pH 7.4.

Serial dilutions by 10 of the Sepharose-bound conjugated were made using a 10% volume to volume suspension of unreacted Sepharose in 25 mM phosphate pH 7.4. The assay system was optimized using the following technique: 100 μl of the Sepharose/Sepharose conjugate dilution, 50 μl of charcoal stripped human serum, and 150,000 cpm of $^{125}$I-anti-thyroxine antibody in 900 μl of 25 mM phosphate buffer, pH 7.4, were mixed. This mixture was incubated at 37° C. for 4 hours with shaking. After incubation the Sepharose was sedimented by centrifugation and the supernatant discarded; 1 ml of 25 mM phosphate buffer was then added. After vortex mixing the Sepharose was again sedimented, the supernatant removed and the radioactivity in the solid phase determined. A Sepharose dilution that yielded approximately 60,000 cpm of radioactivity bound to the solid phase was selected, typically about 1:100,000. Human serum samples having free T4 values already determined by equilibrium dialysis were then assayed using the above Sepharose composition dilution in the optimized assay system. A satisfactory correlation was observed between the method of this invention and equilibrium dialysis.

EXAMPLE 2

In this example the insoluble, differential-binding ligand analogue is a coated plastic test tube rather than a Sepharose conjugate.

Purified L-thyroxine-DSS-BSA from example 1 was coupled to normal mouse immunoglobulins in a modification of the method of Kitagawa and Kanamaru (Kitigawa, T. and Kanamaru, T. in *Enzyme Labelled Immunoassay of Hormones and Drugs*, W. de Gruyter, New York, Berline, 1978, page 59). 1 mg of pure L-thyroxine-DSS-BSA from example 1 was dissolved in 5 ml of 50 mM phosphate buffer pH 7.0. To this was added 75 μl of a 10 mg per milliliter solution of m-maleimidobenzoyl N-hydroxysuccinimide ester [(MBS), Pierce Chemical Co.] ] in tetrahydrofuran. After reaction for 30 minutes at room temperature the mixture was passed down a Sephadex G10 column eluting with 50 mM phosphate buffer. The first proteinacinous fraction to elute was collected, pooled and then degassed by vacuum and equilibrated with nitrogen. 2.0 mg of normal mouse immunoglobulin G prepared from normal mouse serum by the DEAE method of example 1 was dissolved in 2 ml of degassed and nitrogen equilibrated 8 molar urea in 200 mMolar TRIS.HCl buffer, pH 8.6 containing 0.5 mg of dithiothreitol (DITT, Aldrich Chemical Co.). This mixture was stirred for 2 hours at room temperature under nitrogen. After incubation the mixture was applied to a Sephadex G100 column to remove DTT, equilibrated and eluted with degassed and nitrogen equilibrated 200 mM TRIS.HCl. The proteinacious void volume fractions were pooled. The MSB activated antigen solution was made 8M in urea and then mixed with the reduced IgG solution and stirred under nitrogen for 2 hours at room temperature. The resulting solution was dialysed against four changes in 12 hour intervals of 6 liters of 25 mM phosphate buffer pH 7.4. The dialysand was concentrated by ultrafiltration to a final volume of 2.0 ml.

One ml of this solution was serially diluted by ten with phosphate buffer and 1 ml of the dilutions added to polypropylene 12×75 mm test tubes. After sitting for 12 hours, the tubes were aspirated dry and 1.0 ml of a 14 μg/ml normal mouse antibody solution was added to all tubes. After standing for 2 hours the tubes were aspirated and washed with phosphate buffer and allowed to dry.

To each of the coated tubes containing the serial diluted L-thyroxine-DSS-BSA-IgG conjugate was added 50 μl of charcoal stripped human serum and 900 μl of $^{125}$I-labelled anti-thyroxine IgG (150,000 cpm) prepared in example 1.

After incubation at 37° C. for 4 hours the solution was aspirated and the tube bound radioactivity determined. The conjugate dilution which upon coating resulted in about 40% of the 150,000 cpm of $^{125}$I-anti-thyroxine antibodies was chosen and sufficient tubes were coated at this dilution by the method above. A standard curve was generated using these tubes by the addition of 50 μl of human serum free thyroxine standards followed by 900 μl of the $^{125}$I-anti-thyroxine in a fashion identical to that above.

As in example 1, a satisfactory inhibition curve of tracer binding was observed with increasing free thyroxine concentration. Use of this standard curve to measure human samples of known free thyroxine concentrations gave good correlation with known methods.

EXAMPLE 3

This example is similar to example 2 but the developing radioactivity is supplied by a universal second antibody, i.e., one which is species specific for the anti-thyroxine antibody made in the preceding examples.

The tracer for this example was $^{125}$I labelled, goat anti-rabbit-IgG antibody. It was prepared in the following fashion. 10 μg of purified rabbit IgG from example 1 were added to 1 gram of cyanogen bromide activated Sepharose 4B using the method of Cuatrecasas (Cuatrecasas, P., *Loc. Cit.*). The reaction product was suspended in 10 ml of 25 mM phosphate buffer, pH 7.4. 100 μl of goat anti-rabbit-IgG antiserum elicited from goats by standard methods was added to the reaction product suspension. After 72 hours incubation the goat anti-rabbit-IgG antiserum was iodinated and purified in the same fashion as the anti-thyroxine disclosed in example 1.

An assay using this tracer was constructed as follows. To coated tubes coated with optimal L-thyroxnie-DSS-BSA-IgG dilution (example 2) were added 50 μl of charcoal stripped normal human serum and 900 μl of various dilutions in 25 mM Phosphate buffer pH 7.4 of non-radiolabelled, specific anti-thyroxine antibody, purified as in example 1. The tubes were allowed to equilibrate at 32° C. for 4 hours, after which the solutions were removed form the tubes by aspiration. 500,000 cmp of $^{125}$I goat anti-rabbit-IgG in phosphate buffer was added. After 2 hours incubation at 37° C. the liquid was aspirated and the radioactivity associated with the solid phase determined. A dilution of non-radiolabelled, specific anti-thyroxine antibody was found which left ten percent of the goat anti-rabbit-IgG radioactivity bound.

Substitution of the stripped human serum with human serum standards whose free thyroxine concentration was known generated a standard curve with decreased binding of goat $^{125}$I anti-rabbit-IgG with increasing free hormone concentration. Again the method when used to measure patient samples correlated well with a proven reference method for free thyroxine determination.

I claim:

1. A method for determining the amount of free thyroxine in a test sample where the thyroxine is also present bound to endogenous receptors, comprising:
    a. combining the test sample, thyroxine antibody, labelled anti-thyroxine antibody, and unlabelled thyroxine analogue absorbed onto the wall of plastic container, said analogue comprising thyroxine covalently conjugated to a protein in such a fashion that the analogue binds substantially to the thyroxine antibody but binds insubstantially to the endogenous receptors;
    b. incubating to permit the thyroxine and unlabelled thyroxnie analogue to compete for a limited amount of thyroxine antibody;
    c. separating the thyroxine analogue from the residual sample and soluble reagents;
    d. determining the amount of labelled antibody bound to the thyroxine analogue; and
    e. correlating the amount of labelled antibody to the amount of free thyroxine present in the test sample.

2. A method for determining the amount of free ligand in a test sample where the ligand is also present bound to one or more endogenous receptors, comprising:
    a. combining the test sample, ligand receptor and unlabelled differential binding ligand analogue, which analogue is insolubilized and which analogue binds substantially with the ligand receptor but binds insubstantially with endogenous ligand receptors;
    b. incubating said components to permit the free ligand and unlabelled differential binding ligand analogue to compete for the ligand receptor;
    c. separating the unlabelled differential binding ligand analogue;
    d. determining the amount of ligand receptor bound to the ligand or to the unlabelled differential binding ligand analogue; and
    e. correlating the amount of bound ligand receptor to the amount of free ligand present in the test sample.

3. The method of claim 2 wherein the unlabelled, differential binding ligand analogue is insoluble.

4. The method of claim 3 wherein the ligand receptor is an antibody.

5. The method of claim 4 wherein the unlabelled differential binding ligand analogue is made insoluble after it is bound to the ligand.

6. The method of claim 4 wherein the antibody is combined with the test sample and incubated for a sufficient time to bind a substantial amount of free ligand, after which the incubated mixture is combined with the insoluble unlabelled, differential binding ligand analogue.

7. The method of claim 4 wherein the antibody, test sample and unlabelled, differential binding ligand analogue are combined substantially simultaneously.

8. The method of claim 4 wherein the free ligand is determined by contacting it with a labeled receptor capable of binding the ligand.

9. The method of claim 8 wherein the labelled ligand receptor is protein A from *S. aureus* is an antibody.

10. The method of claim 2 wherein the ligand receptor is labelled by covalent substitution with a tracer and the amount of ligand receptor is determined by measuring the amount of the tracer.

11. The method of claim 10 wherein the tracer is a radioisotope.

12. A method for determining the amount of free ligand in a test sample where the ligand is also present bound to one or more endogenous receptors, comprising
    (a) combining the test sample, a labelled ligand receptor which binds said ligand and unlabelled differential binding ligand analogue, said analogue being insolubilized and binding substantially with said ligand receptor, but binding insubstantially with said endogenous receptors for said ligand, said labelled ligand receptor having a dissociation constant, with respect to its binding to analyte, within a factor of ten times more or less than the amount of free analyte;
    (b) incubating said components to permit the free ligand and unlabelled differential binding ligand analogue to compete for said ligand receptor;

(c) separating said unlabelled differential binding ligand analogue bound to said labelled ligand receptor;

(d) determining the amount of said labelled ligand receptor which is bound to the unlabelled differential binding ligand analogue or which is not bound to the unlabelled differential binding ligand analogue; and (e) correlating the amount of bound ligand receptor to the amount of free ligand present in said test sample.

13. A composition for use in the assay of test samples containing free ligand and endogenous receptors for such ligand, comprising the ligand covalently conjugated to a substantially water insoluble substrate or to a water soluble substance physically adsorbed onto a substantially water insoluble substrate, said ligand being conjugated so as to substantially exclude the binding to such insoluble ligand of receptors for such ligand present in said test samples.

14. The composition of claim 13 wherein the water soluble substance comprises a protein.

15. The composition of claim 14 wherein the substrate is a polyolefin surface.

16. The composition of claim 13 wherein the ligand is a hormone or drug.

17. The composition of claim 16 wherein the ligand is a thyroxine.

* * * * *

UNITED STATES PATENT AND TRADEMARK OFFICE
CERTIFICATE OF CORRECTION

PATENT NO. : 5,304,498
DATED : April 19, 1994
INVENTOR(S) : Roger P. Ekins

It is certified that error appears in the above-identified patent and that said Letters Patent is hereby corrected as shown below:

Title page,
Item [57], ABSTRACT,
Line 2, change "ample" to -- sample --.

Column 1,
Line 35, change "sample" to -- samples --.

Column 2,
Line 28, after "assays" insert -- wherever possible. In addition, it would be adventageous to use labelled antibody tracers in such assays --.
Line 42, insert a comma -- , -- after "receptor".

Column 3,
Line 68, change "carboxy" to -- carboxyl --.

Column 4,
Line 10, change "foudn" to -- found --.
Line 12, change "adn" to -- and --.

Column 6,
Line 17, change "antiserumn" to -- antiserum --.
Line 57, change "Bioget P2" to -- Biogel P2 --.

Column 7,
Line 12, change "as" to -- was --.
Line 14, change "boviner" to -- bovine --.

Column 8,
Line 41, change "MSB" to -- MBS --.

Column 9,
Line 58, change "absorbed" to -- adsorbed --.
Line 62, delete "but binds insubstantially to" and insert -- without binding --.
Line 65, change "thyroxnie" to -- thyroxine --.

UNITED STATES PATENT AND TRADEMARK OFFICE
CERTIFICATE OF CORRECTION

PATENT NO. : 5,304,498
DATED : April 19, 1994
INVENTOR(S) : Roger P. Ekins

It is certified that error appears in the above-identified patent and that said Letters Patent is hereby corrected as shown below:

Column 10,
Line 45, after "aureus" insert -- or --.

Signed and Sealed this

Twentieth Day of September, 2005

JON W. DUDAS
*Director of the United States Patent and Trademark Office*